(12) United States Patent
Oremus et al.

(10) Patent No.: US 6,444,691 B1
(45) Date of Patent: Sep. 3, 2002

(54) 1,3-DISUBSTITUTED UREAS AS ACAT INHIBITORS, AND METHOD OF PREPARING THEREOF

(75) Inventors: Vladimír Oremus, Bratislava; Vendelín Šmahovský, Pezinok; Viera Fáberová, Bratislava; Ivan Kakalík, Šenkvice; Ľudmila Schmidtová, Modra; Marián Zemánek, Bratislava, all of (SK)

(73) Assignee: Solvakofarma, a.s., Hlohovec (SK)

( * ) Notice: Subject to any disclaimer, the term of this patent is extended or adjusted under 35 U.S.C. 154(b) by 0 days.

(21) Appl. No.: 09/581,821

(22) PCT Filed: Dec. 16, 1998

(86) PCT No.: PCT/SK98/00019

§ 371 (c)(1),
(2), (4) Date: Jul. 10, 2000

(87) PCT Pub. No.: WO99/32437

PCT Pub. Date: Jul. 1, 1999

(30) Foreign Application Priority Data

Dec. 19, 1997 (SK) .......................................... PV 1751-97

(51) Int. Cl.⁷ .......................... A61K 31/44; A61K 31/17
(52) U.S. Cl. ....................... 514/353; 514/597; 546/306; 564/49; 564/50
(58) Field of Search ..................... 564/49, 50; 546/306; 514/353, 597

(56) References Cited

U.S. PATENT DOCUMENTS

| | | | |
|---|---|---|---|
| 3,284,433 A | * 11/1966 | Becker et al. | 260/96.5 |
| 3,933,814 A | * 1/1976 | Haberkorn et al. | 260/248 NS |
| 5,008,456 A | * 4/1991 | Murata et al. | 564/322 |
| 5,219,859 A | 6/1993 | Festal et al. | 514/269 |

FOREIGN PATENT DOCUMENTS

| | | | |
|---|---|---|---|
| DE | 1802739 | * | 6/1969 |
| EP | 0709225 | * | 6/1969 |
| EP | 0 506 532 | | 9/1992 |
| EP | 0 665 216 | | 8/1995 |
| EP | 0 709 225 | | 6/1996 |
| FR | 2 674 522 | | 10/1992 |
| JP | 5-097802 | | 4/1993 |
| JP | 7-258199 | | 10/1995 |

* cited by examiner

*Primary Examiner*—Peter O'Sullivan
(74) *Attorney, Agent, or Firm*—Oblon, Spivak, McClelland, Maier & Neustadt, P.C.

(57) ABSTRACT

The invention relates to 1,3-disubstituted ureas of general formula (I) where $R^1$ is an aryl, $R^2$ is nitro and/or amino, and X is oxygen and/or sulfur, and the method of preparing thereof which consists in treating aromatic amines with isocyanates. Isocyanates may be formed in situ and the reaction carried out in toluene, at 80° C. If the nitro group is formed, it is reduced with hydrogen in the presence of palladium catalyst to the amino group. The obtained 1,3-disubstituted ureas are inhibitors of the activity of the acyl co-enzyme A: cholesterol acyltransferase (ACAT) enzyme, and may be used to inhibit cholesterol esterification and absorption in hypercholesterolemia.

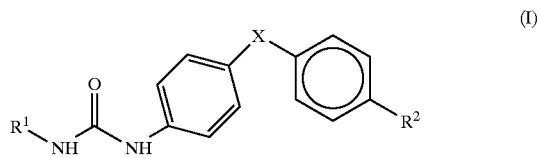

(I)

5 Claims, No Drawings

1,3-DISUBSTITUTED UREAS AS ACAT INHIBITORS, AND METHOD OF PREPARING THEREOF

TECHNICAL FIELD

The invention relates to compounds the principal characteristics of which include inhibition of the acyl-coenzyme A: cholesterol acyltransferase (ACAT) enzyme activity, and to a method for the preparation of such compounds.

BACKGROUND ART

The acyl-coenzyme A: cholesterol O-acyltransferase (EC 2.3.1.26) (ACAT) enzyme is responsible for the catalysis of the intracellular esterification of cholesterol. ACAT is present in most tissues such as the intestine, liver, and arterial wall. The enzyme is assumed to be involved in numerous processes which underlie the development of atherosclerosis, absorption of dietary cholesterol, accumulation of cholesterol esters, hepatic secretion of cholesterol esters into the blood plasma in the form of VLDL cholesterol.

A number of substances of the urea type have been described to inhibit ACAT. We shall show several more, recent examples describing 1,3-disubstituted ureas as ACAT enzyme inhibitors. Patents EP 506532, FR 2674522, JP 93097802, U.S. Pat. No. 5,219,859 describe ureas containing indole derivatives in their molecules. A combination of aromatic and aliphatic moieties has been described in Patents EP 665216, JP 95258199. Introduction into the molecule of a 1,3-dioxolane ring has been reported in Bioorg. Med. Chem. Lett. 1995, 5(15): 1581.

Despite the fact, the some 1,3-disubstituted ureas of the similar structure have been described in U.S. Pat. No. 3,284,433 as anticoccidial agents and one compound of similar structure is mentioned in patent application EP 0709225 as color developing agent, 1,3-disubstituted ureas of the present invention have not been described in literature yet.

DISCLOSURE OF INVENTION 1,3-Disubstituted ureas of general formula I,

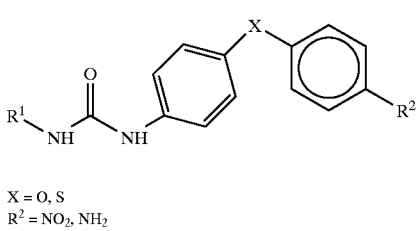

$X = O, S$
$R^2 = NO_2, NH_2$ wherein $R^1$ is 2-fluorophenyl, 2,4-difluorophenyl, 2,5-difluorophenyl, 2,6-difluorophenyl, 2-chlorophenyl, 2,3-dichlorophenyl, 2,6-dichlorophenyl, 3,5-dichlorophenyl, 2-methylphenyl, 4-methylphenyl, 2,4-dimethylphenyl, 2,6-dimethylphenyl, 3,5-dimethylphenyl, 2,6-di(methylethyl) phenyl, 2-trifluoromethylphenyl, 3-trifluoromethylphenyl, 4-trifluoromethylphenyl, 2-pyridyl, 3-pyridyl, 4-pyridyl, 1-naphthyl, 2-naphthyl, 1-adamantyl, and $R^2$ is nitro, and X=O,
wherein $R^1$ is 4-nitrophenyl, 2-fluorophenyl, 4-fluorophenyl, 2,4-difluorophenyl, 2,5-difluorophenyl, 2,6-difluorophenyl, 2-chlorophenyl, 4-chlorophenyl, 2,3-dichlorophenyl, 2,4-dichlorophenyl, 2,6-dichlorophenyl, 3,4-dichlorophenyl, 3,5-dichlorophenyl, 2-methylphenyl, 4-methylphenyl, 2,4-dimethylphenyl, 2,6-dimethylphenyl, 3,5-dimethylphenyl, 2,6-di(methylethyl)phenyl, 2-trifluoromethylphenyl, 3-trifluoromethylphenyl, 4-trifluoromethylphenyl, 2-pyridyl, 3-pyridyl, 4-pyridyl, 1-naphthyl, 2-naphthyl, 1-adamantyl, and $R^2$ is nitro, and X=S;
and for $R^1$ being 2,4-difluorophenyl, 2,3-dichlorophenyl, 2,6-dimethylphenyl, 2,6-di(methylethyl)-phenyl $R^2$ is amino, and X=O, S.

The method for the preparation of the above compounds according to this invention consists in reacting an isocyanate (as prepared in situ or as commercially available) with amine to give an urea the nitro group of which may subsequently be reduced to the amino group. Ureas prepared in this way show inhibitory effect on acyl-coenzyme A: cholesterol acyltransferase (ACAT).

EXAMPLES

Example 1

1-(2-Fluorophenyl)-3-((4'-nitrophenoxy)-phenyl)-urea

A solution of 2-fluorophenylisocyanate (1.1 equiv.) in diethylether (20 ml) is added dropwise to a solution of 4'-nitrophenoxy-aniline (2.30 g, 0.01 mol) in a mixture of diethylether (20 ml) and tetrahydrofurane (20 ml) at laboratory temperature, and the mixture is stirred through a night. The precipitated product is aspirated, washed with diethylether (20 ml). The raw product is purified by chromatography on silica gel eluting with dichloromethane-methanol.

Analysis for $C_{19}H_{14}FN_3O_4$

| % C(calcd/found) | % H | % N |
|---|---|---|
| 62.11/62.09 | 3.84/3.88 | 11.44/11.29 |

Yield: 48% Melting temp.: 253–255° C.

Example 2

1-(2,4-Difluorophenyl)-3-((4'-nitrophenoxy-phenyl)-urea

The title compound was prepared from 2,4-difluorophenylisocyanate by an analogous procedure to that described in Example 1.

$^1$H-NMR (CDCl$_3$): 6.98–7.18(m, 5H, H-arom.); 7.23–7.37(m, 1H, H-arom.); 7.56(d, 2H, H-arom.); 8.03–8.16(m, 1H, H-arom.); 8.24(d, 2H, H-arom.); 8.50(s, 1H, NH); 9.13(s, 1H, NH).

$^{13}$C-NMR (CDCl$_3$): 103.72(CH-arom.); 110.96(CH-arom.); 116.73(CH-arom.); 119.88(CH-arom.); 121.18(CH-arom.); 122.02(CH-arom.); 126.09(CH-arom.); 136.94, 141.91, 148.48, 152.27, 154.49, 159.80(C-arom.); 163.46 (C=O).

Analysis for $C_{19}H_{13}F_2N_3O_4$

| % C(calcd/found) | % H | % N |
|---|---|---|
| 59.22/59.20 | 3.40/3.53 | 10.91/10.89 |

Yield: 85% Melting temp.: 223–224° C.

Example 3

1-(2,5-Difluorophenyl)-3-((4'-nitrophenoxy)-phenyl)-urea

The title compound was prepared from 2,5-difluorophenylisocyanate by an analogous procedure to that described in Example 1.

¹H-NMR (CDCl₃): 6.73–6.88(m, 1H, H-arom.); 7.04–7.35(m, 5H, H-arom.); 7.56(d, 2H, H-arom.); 7.98–8.11(m, 1H, H-arom.); 8.22(d, 2H, H-arom.); 8.75–9.30(br.s., 2H, NH).

¹³C-NMR (CDCl₃): 106.56(CH-arom.); 107.75(CH-arom.); 115.67(CH-arom.); 116.74(CH-arom.); 120.03(CH-arom.); 121.21(CH-arom.); 126.08(CH-arom.); 128.82, 136.62, 141.95, 148.73, 151.95, 155.65, 160.38(C-arom.); 163.42(C=O).

Analysis for $C_{19}H_{13}F_2N_3O_4$

| % C(calcd/found) | % H | % N |
|---|---|---|
| 59.22/59.07 | 3.40/3.49 | 10.91/10.83 |

Yield: 76% Melting temp.: 207–208° C.

Example 4
1-(2,6-Difluorophenyl)-3-((4'-nitrophenoxy)-phenyl)-urea

The title compound was prepared from 2,6-difluorophenylisocyanate by an analogous procedure to that described in Example 1.

¹H-NMR (CDCl₃): 6.95–7.26(m, 6H, H-arom.); 7.42–7.56(m, 2H, H-arom.); 8.01–8.23(m, 3H, H-arom.); 8.94–9.05(m, 2H, NH).

¹³C-NMR (CDCl₃): 111.77(CH-arom.); 116.82(CH-arom.); 120.06(CH-arom.); 121.18(CH-arom.); 126.19(CH-arom.); 127.11(CH-arom.); 137.31, 141.99, 148.49, 152.61, 155.65, 160.57(C-arom.); 163.61(C=O).

Analysis for $C_{19}H_{13}F_2N_3O_4$

| % C(calcd/found) | % H | % N |
|---|---|---|
| 59.22/59.10 | 3.40/3.55 | 10.91/10.78 |

Yield: 75% Melting temp.: 231–232° C.

Example 5
1-(2-Chlorophenyl)-3-((4'-nitrophenoxy)-phenyl)-urea

The title compound was prepared from 2-chlorophenylisocyanate by an analogous procedure to that described in Example 1.

Analysis for $C_{19}H_{14}ClN_3O_4$

| % C(calcd/found) | % H | % N | % Cl |
|---|---|---|---|
| 59.46/59.37 | 3.68/3.82 | 10.95/10.78 | 9.24/8.99 |

Yield: 63% Melting temp.: 195–197° C.

Example 6
1-(2,3-Dichlorohenyl)-3-((4'-nitrophenoxy)-phenyl)-urea

The title compound was prepared from 2,3-dichlorophenylisocyanate by an analogous procedure to that described in Example 1.

Analysis for $C_{19}H_{13}Cl_2N_3O_4$

| % C(calcd/found) | % H | % N | % Cl |
|---|---|---|---|
| 54.56/54.50 | 3.13/3.31 | 10.05/9.78 | 16.95/16.91 |

Yield: 74% Melting temp.: 199–201° C.

Example 7
1-(2,6-Dichlorophenyl)-3-((4'-nitrophenoxy)-phenyl)-urea

The title compound was prepared from 2,6-dichlorophenylisocyanate by an analogous procedure to that described in Example 1.

Analysis for $C_{19}H_{13}Cl_2N_3O_4$

| % C(calcd/found) | % H | % N | % Cl |
|---|---|---|---|
| 54.56/54.39 | 3.13/3.20 | 10.05/9.92 | 16.95/16.81 |

Yield: 68% Melting temp.: 195–198° C.

Example 8
1-(3,5-Dichlorophenyl)-3-((4'-nitrophenoxy)-phenyl)-urea

The title compound was prepared from 3,5-dichlorophenylisocyanate by an analogous procedure to that described in Example 1.

Analysis for $C_{19}H_{13}Cl_2N_3O_4$

| % C(calcd/found) | % H | % N | % Cl |
|---|---|---|---|
| 54.56/54.48 | 3.13/3.30 | 10.05/10.01 | 16.95/17.24 |

Yield: 56% Melting temp.: 213–216° C.

Example 9
1-(2-Methylphenyl-3-((4'-nitrophenoxy)-phenyl)-urea

The title compound was prepared from 2-methylphenylisocyanate by an analogous procedure to that described in Example 1.

Analysis for $C_{20}H_{17}N_3O_4$

| % C(calcd/found) | % H | % N |
|---|---|---|
| 60.11/65.96 | 4.72/4.89 | 11.56/11.48 |

Yield: 59% Melting temp.: 112–116° C.

Example 10
1-(4-Methylphenyl)-3-((4'-nitrophenoxy)-phenyl)-urea

The title compound was prepared from 4-methylphenylisocyanate by an analogous procedure to that described in Example 1.

Analysis for $C_{20}H_{17}N_3O_4$

| % C(calcd/found) | % H | % N |
|---|---|---|
| 66.11/66.02 | 4.72/4.87 | 11.56/11.40 |

Yield: 64% Melting temp.: 168–170° C.

Example 11
1-(2,4-Dimethylphenyl)-3-((4'-nitrophenoxy)-phenyl)-urea

The title compound was prepared from 2,4-dimethylphenylisocyanate by an analogous procedure to that described in Example 1.

Analysis for $C_{21}H_{19}N_3O_4$

| % C(calcd/found) | % H | % N |
| --- | --- | --- |
| 66.83/66.87 | 5.07/5.10 | 11.13/11.05 |

Yield: 73% Melting temp.: 165–169° C.

Example 12

1-(2,6-Dimethylphenyl)-3-((4'-nitrophenoxy)-phenyl)-urea

The title compound was prepared from 2,6-dimethylphenylisocyanate by an analogous procedure to that described in Example 1.

$^1$H-NMR (CDCl$_3$): 2.22(s, 6H, CH$_3$); 7.04–7.17(m, 7H, H-arom.); 7.57(m, 2H, H-arom.); 7.74(s, 1H, NH); 8.23(d, 2H, H-arom.); 8.87(s, 1H, NH).

$^{13}$C-NMR (CDCl$_3$): 18.19(2x, CH$_3$); 116.61(CH-arom.); 119.54(CH-arom.); 121.08(CH-arom.); 126.07(CH-arom.); 127.67(CH-arom.); 135.53(CH-arom.); 125.93, 135.51, 137, 95, 141.82, 147,87, 153.10(CH-arom.); 163.64(C=O).

Analysis for C$_{21}$H$_{19}$N$_3$O$_4$

| % C(calcd/found) | % H | % N |
| --- | --- | --- |
| 66.83/66.67 | 5.07/5.18 | 11.13/10.98 |

Yield: 68% Melting temp.: 249–250° C.

Example 13

1-(3,5-Dimethylphenyl)-3-((4'-nitrophenoxy)-phenyl)-urea

The title compound was prepared from 3,5-dimethylphenylisocyanate by an analogous procedure to that described in Example 1.

Analysis for C$_{21}$H$_{19}$N$_3$O$_4$

| % C(calcd/found) | % H | % N |
| --- | --- | --- |
| 66.83/66.78 | 5.07/5.22 | 11.13/11.06 |

Yield: 58% Melting temp.: 145–147° C.

Example 14

1-(2,6-Di-(methylethyl)-phenyl)-3-((4'-nitrophenoxy)-phenyl)-urea

The title compound was prepared from 2,6-di-(methylethyl)phenylisocyanate by an analogous procedure to that described in Example 1.

$^1$H-NMR (CDCl$_3$): 1.18(d, 6H, 2xCH$_3$); 3.22(hept., 2H, 2xCH); 7.06–7.30(m, 7H, H-arom.); 7.56(d, 2H, H-arom.); 7.63(s, 1H, NH); 8.23(d, 2H, H-arom.); 8.78(s, 1H, NH).

$^{13}$C-NMR (CDCl$_3$): 23.31(2xCH$_3$); 27.86(2xCH); 116.58 (CH-arom.); 119.44(CH-arom.); 120.86(CH-arom.); 122.72 (CH-arom.); 125.87(CH-arom.); 146.53(CH-arom.); 127.08, 132.14, 137.80, 141.83, 147,89, 154.10(C-arom.); 163.46(C=O).

Analysis for C$_{25}$H$_{27}$N$_3$O$_4$

| % C(calcd/found) | % H | % N |
| --- | --- | --- |
| 69.27/69.13 | 6.28/6.34 | 9.69/9.56 |

Yield: 88% Melting temp.: 208–210° C.

Example 15

1-(2-Trifluoromethylphenyl)-3-((4'-nitrophenoxy)-phenyl)-urea

4'-Nitrophenoxy-aniline (1.0 g, 4.3 mmol), triphosgene (0.43 g, 1.44 mmol), triethylamine (0.6 ml, 4.3 mmol) are heated in toluene (15 ml) in a pressure tube at 80° C. for 20 hours. Then, 2-trifluoromethylaniline (0.53 ml, 4.3 mmol) and triethylamine (0.6 ml, 4.3 mmol) in toluene (10 ml) are added. The mixture is heated at 80° C. for 4 hours, then it is concentrated, and the product is isolated using chromatography on silica gel eluting with dichloromethane-methanol.

Analysis for C$_{20}$H$_{14}$F$_3$N$_3$O$_4$

| % C(calcd/found) | % H | % N |
| --- | --- | --- |
| 57.56/57.60 | 3.38/3.44 | 10.07/9.89 |

Yield: 67% Melting temp.: 201–203° C.

Example 16

1-(3-Trifluoromethylphenyl)-3-((4'-nitrophenoxy)-phenyl)-urea

The title compound was prepared from 3-trifluoromethylaniline by an analogous procedure to that described in Example 15.

Analysis for C$_{20}$H$_{14}$F$_3$N$_3$O$_4$

| % C(calcd/found) | % H | % N |
| --- | --- | --- |
| 57.56/57.66 | 3.38/3.45 | 10.07/9.96 |

Yield: 72% Melting temp.: 208–211° C.

Example 17

1-(4-Trifluoromethylphenyl)-3-((4'-nitrophenoxy)-phenyl)-urea

The title compound was prepared from 4-trifluoromethylaniline by an analogous procedure to that described in Example 15.

Analysis for C$_{20}$H$_{14}$F$_3$N$_3$O$_4$

| % C(calcd/found) | % H | % N |
| --- | --- | --- |
| 57.56/57.48 | 3.38/3.41 | 10.07/10.00 |

Yield: 45% Melting temp.: 185–189° C.

Example 18

1-(2-Pyridyl)-3-(4'-nitrophenoxy)-phenyl)-urea

The title compound was prepared from 2-pyridylamine by an analogous procedure to that described in Example 15.

Analysis for C$_{18}$H$_{14}$N$_4$O$_4$

| % C(calcd/found) | % H | % N |
| --- | --- | --- |
| 61.71/61.67 | 4.03/4.06 | 15.99/15.79 |

Yield: 76% Melting temp.: 143–146° C.

Example 19
1-(3-Pyridyl)-3-(4'-nitrophenoxy)-phenyl)-urea

The title compound was prepared from 3-pyridylamine by an analogous procedure to that described in Example 15.

Analysis for $C_{18}H_{14}N_4O_4$

| % C(calcd/found) | % H | % N |
|---|---|---|
| 61.71/61.58 | 4.03/4.21 | 15.99/15.87 |

Yield: 69% Melting temp.: 177–179° C.

Example 20
1-(4-Pyridyl)-3-(4'-nitrophenoxy)-phenyl)-urea

The title compound was prepared from 4-pyridylamine by an analogous procedure to that described in Example 15.

Analysis for $C_{18}H_{14}N_4O_4$

| % C(calcd/found) | % H | % N |
|---|---|---|
| 61.71/61.66 | 4.03/4.11 | 15.99/15.87 |

Yield: 72% Melting temp.: 126–127° C.

Example 21
1-(1-Naphthyl)-3-(4'-nitrophenoxy)-phenyl)-urea

The title compound was prepared from 1-naphthylisocyanate by an analogous procedure to that described in Example 1.

Analysis for $C_{23}H_{17}N_3O_4$

| % C(calcd/found) | % H | % N |
|---|---|---|
| 69.17/69.23 | 4.29/4.41 | 10.52/10.46 |

Yield: 82% Melting temp.: 117–119° C.

Example 22
1-(2-Naphthyl)-3-(4'-nitrophenoxy)-phenyl)-urea

The title compound was prepared from 2-naphthylamine by an analogous procedure to that described in Example 15.

Analysis for $C_{23}H_{17}N_3O_4$

| % C(calcd/found) | % H | % N |
|---|---|---|
| 69.17/69.09 | 4.29/4.36 | 10.52/10.38 |

Yield: 69% Melting temp.: 103–106° C.

Example 23
1-(1-Adamantyl)-3-(4'-nitrophenoxy)-phenyl)-urea

The title compound was prepared from 1-adamantylamine by an analogous procedure to that described in Example 15.

Analysis for $C_{23}H_{25}N_3O_4$

| % C(calcd/found) | % H | % N |
|---|---|---|
| 67.80/67.65 | 6.18/6.23 | 10.31/10.16 |

Yield: 61% Melting temp.: 143–146° C.

Example 24
1-(4-Nitrophenyl)-3-((4'-nitrophenylthio)-phenyl)-urea

A solution of 4-nitrophenylisocyanate in diethylether (20 ml) is added dropwise to a solution of 4'-nitrophenylthio-aniline (2.46, g, 0.01 mol) in a mixture of diethylether (20 ml) and tetrahydrofurane (20 ml) at laboratory temperature, and the mixture is stirred for 16 hours. The resulting product is aspirated, washed with diethylether (20 ml). The crude product is purified by chromatography on silica gel eluting with dichloromethane and methanol.

Analysis for $C_{19}H_{14}N_4O_5S$

| % C (calcd/found) | % H | % N | S % |
|---|---|---|---|
| 55.61/55.52 | 3.44/3.49 | 13.65/13.59 | 7.81/7.67 |

Yield: 56% Melting temp.: 164–167° C.

Example 25
1-(2-Fluorophenyl)-3-((4'-nitrophenylthio)-phenyl)-urea

The title compound was prepared from 2-fluorophenylisocyanate by an analogous procedure to that described in Example 24.

Analysis for $C_{19}H_{14}FN_3O_3S$

| % C (calcd/found) | % H | % N | S % |
|---|---|---|---|
| 59.52/59.41 | 3.68/3.77 | 10.96/11.04 | 8.36/8.41 |

Yield: 61% Melting temp.: 274–277° C.

Example 26
1-(4-Fluorophenyl)-3-((4'-nitrophenylthio)-phenyl)-urea

The title compound was prepared from 4-fluorophenylisocyanate by an analogous procedure to that described in Example 24.

Analysis for $C_{19}H_{14}FN_3O_3S$

| % C (calcd/found) | % H | % N | S % |
|---|---|---|---|
| 59.52/59.46 | 3.68/3.71 | 10.96/10.87 | 8.36/8.18 |

Yield: 59% Melting temp.: 287–290° C.

Example 27
1-(2,4-Difluorophenyl)-3-((4'-nitrophenylthio)-phenyl)-urea

The title compound was prepared from 2,4-difluorophenylisocyanate by an analogous procedure to that described in Example 24.

Analysis for $C_{19}H_{13}F_2N_3O_3S$

| % C (calcd/found) | % H | % N | S % |
|---|---|---|---|
| 56.86/56.78 | 3.26/3.39 | 10.47/10.41 | 7.99/7.86 |

Yield: 57% Melting temp.: 268–271° C.

Example 28
1-(2,5-Difluorophenyl)-3-((4'-nitrophenylthio)-phenyl)-urea

The title compound was prepared from 2,5-difluorophenylisocyanate by an analogous procedure to that described in Example 24.

Analysis for $C_{19}H_{13}F_2N_3O_3S$

| % C (calcd/found) | % H | % N | S % |
|---|---|---|---|
| 56.86/56.76 | 3.26/3.37 | 10.47/10.35 | 7.99/8.05 |

Yield: 64% Melting temp.: 259–261° C.

Example 29
1-(2,6-Difluorophenyl)-3-((4'-nitrophenylthio)-phenyl)-urea

The title compound was prepared from 2,6-difluorophenylisocyanate by an analogous procedure to that described in Example 24.

Analysis for $C_{19}H_{13}F_2N_3O_3S$

| % C (calcd/found) | % H | % N | S % |
|---|---|---|---|
| 56.86/56.69 | 3.26/3.34 | 10.47/10.43 | 7.99/7.81 |

Yield: 68% Melting temp.: 263–265°C.

Example 30
1-(2-Chlorophenyl)-3-((4'-nitrophenylthio)-phenyl)-urea

The title compound was prepared from 2-chlorophenylisocyanate by an analogous procedure to that described in Example 24.

Analysis for $C_{19}H_{14}ClN_3O_3S$

| % C (calcd/found) | % H | % N | % Cl | S % |
|---|---|---|---|---|
| 57.07/57.01 | 3.53/3.62 | 10.51/11.46 | 8.87/8.65 | 8.02/7.95 |

Yield: 65% Melting temp.: 231–233° C.

Example 31
1-(4-Chlorophenyl)-3-((4'-nitrophenylthio)-phenyl)-urea

The title compound was prepared from 4-chlorophenylisocyanate by an analogous procedure to that described in Example 24.

Analysis for $C_{19}H_{14}ClN_3O_3S$

| % C (calcd/found) | % H | % N | % Cl | S % |
|---|---|---|---|---|
| 57.07/56.97 | 3.53/3.57 | 10.51/10.45 | 8.87/8.81 | 8.02/7.86 |

Yield: 63% Melting temp.: 206–209° C.

Example 32
1-(2,3-Dichlorophenyl)-3-((4'-nitrophenylthio)-phenyl)-urea

The title compound was prepared from 2,3-dichlorophenylisocyanate by an analogous procedure to that described in Example 24.

Analysis for $C_{19}H_{13}Cl_2N_3O_3S$

| % C (calcd/found) | % H | % N | % Cl | S % |
|---|---|---|---|---|
| 52.55/52.46 | 3.02/3.07 | 9.68/9.62 | 16.33/16.27 | 7.38/7.50 |

Yield: 75% Melting temp.: 157–159° C.

Example 33
1-(2,4-Dichlorophenyl)-3-((4'-nitrophenylthio)-phenyl)-urea

The title compound was prepared from 2,4-dichlorophenylisocyanate by an analogous procedure to that described in Example 24.

Analysis for $C_{19}H_{13}Cl_2N_3O_3S$

| % C (calcd/found) | % H | % N | % Cl | S % |
|---|---|---|---|---|
| 52.55/52.57 | 3.02/3.21 | 9.68/9.54 | 16.33/16.35 | 7.38/7.28 |

Yield: 57% Melting temp.: 174–178° C.

Example 34
1-(2,6-Dichlorophenyl)-3-((4'-nitrophenylthio)-phenyl)-urea

The title compound was prepared from 2,6-dichlorophenylisocyanate by an analogous procedure to that described in Example 24.

Analysis for $C_{19}H_{13}Cl_2N_3O_3S$

| % C (calcd/found) | % H | % N | % Cl | S % |
|---|---|---|---|---|
| 52.55/52.51 | 3.02/3.07 | 9.68/9.73 | 16.33/16.25 | 7.38/7.19 |

Yield: 83% Melting temp.: 164–167° C.

Example 35
1-(3,4-Dichlorophenyl)-3-((4'-nitrophenylthio)-phenyl)-urea

The title compound was prepared from 3,4-dichlorophenylisocyanate by an analogous procedure to that described in Example 24.

Analysis for $C_{19}H_{13}Cl_2N_3O_3S$

| % C (calcd/found) | % H | % N | % Cl | S % |
|---|---|---|---|---|
| 52.55/52.47 | 3.02/3.14 | 9.68/9.57 | 16.33/16.09 | 7.38/7.24 |

Yield: 57% Melting temp.: 238–240° C.

Example 36
1-(3,5-Dichlorophenyl)-3-((4'-nitrophenylthio)-phenyl)-urea

The title compound was prepared from 3,5-dichlorophenylisocyanate by an analogous procedure to that described in Example 24.

Analysis for $C_{19}H_{13}Cl_2N_3O_3S$

| % C (calcd/found) | % H | % N | % Cl | S % |
|---|---|---|---|---|
| 52.55/52.47 | 3.02/3.11 | 9.68/9.59 | 16.33/16.21 | 7.38/7.41 |

Yield: 67% Melting temp.: 185–188° C.

Example 37
1-(2-Methylphenyl)-3-((4'-nitrophenylthio)-phenyl)-urea

The title compound was prepared from 2-methylphenylisocyanate by an analogous procedure to that described in Example 24.

Analysis for $C_{20}H_{17}N_3O_3S$

| % C (calcd/found) | % H | % N | S % |
|---|---|---|---|
| 63.31/63.22 | 4.52/4.66 | 11.07/10.79 | 8.45/8.34 |

Yield: 78% Melting temp.: 229–234° C.

Example 38

1-(4-Methylphenyl)-3-((4'-nitrophenylthio)-phenyl)-urea

The title compound was prepared from 4-methylphenylisocyanate by an analogous procedure to that described in Example 24.

Analysis for $C_{20}H_{17}N_3O_3S$

| % C (calcd/found) | % H | % N | S % |
|---|---|---|---|
| 63.31/63.25 | 4.52/4.63 | 11.07/11.12 | 8.45/8.35 |

Yield: 73% Melting temp.: 163–166° C.

Example 39

1-(2,4-Dimethylphenyl)-3-((4'-nitrophenylthio)-phenyl)-urea

The title compound was prepared from 2,4-dimethylphenylisocyanate by an analogous procedure to that described in Example 24.

Analysis for $C_{20}H_{19}N_3O_3S$

| % C (calcd/found) | % H | % N | S % |
|---|---|---|---|
| 64.11/64.08 | 4.87/4.83 | 10.68/10.59 | 8.15/7.95 |

Yield: 65% Melting temp.: 209–213° C.

Example 40

1-(2,6-Dimethylphenyl)-3-((4'-nitrophenylthio)-phenyl)-urea

The title compound was prepared from 2,6-dimethylphenylisocyanate by an analogous procedure to that described in Example 24.

Analysis for $C_{20}H_{19}N_3O_3S$

| % C (calcd/found) | % H | % N | S % |
|---|---|---|---|
| 64.11/63.97 | 4.87/4.83 | 10.68/10.47 | 8.15/8.01 |

Yield: 72% Melting temp.: 264–267° C.

Example 41

1-(3,5-Dimethylphenyl)-3-((4'-nitrophenylthio)-phenyl)-urea

The title compound was prepared from 3,5-dimethylphenylisocyanate by an analogous procedure to that described in Example 24.

Analysis for $C_{21}H_{19}N_3O_3S$

| % C(calcd/found) | % H | % N | S % |
|---|---|---|---|
| 64.11/64.04 | 4.87/4.99 | 10.68/10.63 | 8.15/8.01 |

Yield: 68% Melting temp.: 194–196° C.

Example 42

1-(2,6-Di-(methylethyl)-phenyl-((4'-nitrophenylthio)-phenyl)-urea

The title compound was prepared from 2,6-(methylethyl)-phenylisocyanate by an analogous procedure to that described in Example 24.

Analysis for $C_{25}H_{27}N_3O_3S$

| % C(calcd/found) | % H | % N | S % |
|---|---|---|---|
| 66.79/66.72 | 6.06/6.17 | 9.35/9.27 | 7.12/6.96 |

Yield: 72% Melting temp.: 175–177° C.

Example 43

1-(2-Trifluoromethylphenyl)-3-((4'-nitrophenylthio)-phenyl)-urea

4'-Nitrophenylthio-aniline (1.06 g, 4.3 mmol), triphosgene (0.43 g, 1.44 mmol), triethylamine (0.6 g, 4.3 mmol) in toluene (15 ml) are heated in a pressure tube at 80° C. for 20 hours. Subsequently, 2-trifluoromethylaniline (0.53 ml, 4.3 mmol) and triethylamine (0.6 ml, 4.3 mmol) in toluene (10 ml) are added. The mixture is heated at 80° C. for 4 hours, then concentrated, and the product is separated by chromatography on silica gel eluting with dichloromethane-methanol.

Analysis for $C_{20}H_{14}F_3N_3O_3S$

| % C(calcd/found) | % H | % N | S % |
|---|---|---|---|
| 55.43/55.38 | 3.26/3.39 | 9.70/9.71 | 7.40/7.35 |

Yield: 52% Melting temp.: 257–261° C.

Example 44

1-(3-Trifluoromethylphenyl)-3-((4'-nitrophenylthio)-phenyl)-urea

The title compound was prepared from 3-trifluorophenylisocyanate by an analogous procedure to that described in Example 43.

Analysis for $C_{20}H_{14}F_3N_3O_3S$

| % C(calcd/found) | % H | % N | S % |
|---|---|---|---|
| 55.43/55.21 | 3.26/3.38 | 9.70/9.53 | 7.40/7.31 |

Yield: 65% Melting temp.: 241–244° C.

Example 45

1-(4-Trifluoromethylphenyl)-3-((4'-nitrophenylthio)-phenyl)-urea

The title compound was prepared from 4-trifluorophenylisocyanate by an analogous procedure to that described in Example 43.

Analysis for $C_{20}H_{14}F_3N_3O_3S$

| % C(calcd/found) | % H | % N | S % |
|---|---|---|---|
| 55.43/55.37 | 3.26/3.33 | 9.70/9.81 | 7.40/7.28 |

Yield: 51% Melting temp.: 254–257° C.

Example 46

1-(2-Pyridyl)-3-((4'-nitrophenylthio)-phenyl)-urea

The title compound was prepared from 2-pyridylamine by an analogous procedure to that described in Example 43.

Analysis for $C_{18}H_{14}N_4O_3S$

| % C(calcd/found) | % H | % N | S % |
|---|---|---|---|
| 59.01/58.86 | 3.85/3.91 | 15.29/15.23 | 8.75/8.80 |

Yield: 48% Melting temp.: 278–281° C.

Example 47

1-(3-Pyridyl)-3-((4'-nitrophenylthio)-phenyl)-urea

The title compound was prepared from 3-pyridylamine by an analogous procedure to that described in Example 43.

Analysis for $C_{18}H_{14}N_4O_3S$

| % C(calcd/found) | % H | % N | S % |
|---|---|---|---|
| 59.01/58.99 | 3.85/3.99 | 15.29/15.25 | 8.75/8.49 |

Yield: 63% Melting temp.: 261–264° C.

Example 48

1-(4-Pyridyl)-3-((4'-nitrophenylthio)-phenyl)-urea

The title compound was prepared from 4-pyridylamine by an analogous procedure to that described in Example 43.

Analysis for $C_{18}H_{14}N_4O_3S$

| % C(calcd/found) | % H | % N | S % |
|---|---|---|---|
| 59.01/58.92 | 3.85/3.76 | 15.29/15.32 | 8.75/8.67 |

Yield: 69% Melting temp.: 190–192° C.

Example 49

1-(1-Naphthyl)-3-((4'-nitrophenylthio)-phenyl)-urea

The title compound was prepared from 1-naphthylisocyanate by an analogous procedure to that described in Example 24.

Analysis for $C_{23}H_{17}N_3O_3S$

| % C(calcd/found) | % H | % N | S % |
|---|---|---|---|
| 66.49/66.53 | 4.13/4.21 | 10.12/10.17 | 7.70/7.54 |

Yield: 56% Melting temp.: 164–168° C.

Example 50

1-(2-Naphthyl)-3-((4'-nitrophenylthio)-phenyl)-urea

The title compound was prepared from 2-naphthylamine by an analogous procedure to that described in Example 43.

Analysis for $C_{23}H_{17}N_3O_3S$

| % C(calcd/found) | % H | % N | S % |
|---|---|---|---|
| 66.49/66.47 | 4.13/4.25 | 10.12/10.06 | 7.70/7.57 |

Yield: 69% Melting temp.: 142–147° C.

Example 51

1-(1-Adamantyl)-3-((4'-nitrophenylthio)-phenyl)-urea

The title compound was prepared from 1-adamantylamine by an analogous procedure to that described in Example 43.

Analysis for $C_{23}H_{25}N_3O_3S$

| % C(calcd/found) | % H | % N | S % |
|---|---|---|---|
| 65.22/65.17 | 5.95/6.03 | 9.93/10.02 | 7.56/7.38 |

Yield: 52% Melting temp.: 264–267° C.

Example 52

1-(2,4-Difluorophenyl)-3-((4'-aminophenoxy)-phenyl)-urea

One gram of compound 2 is dissolved in methanol (20 ml) and 0.1 g of 10% palladium on charcoal is added. The mixture is stirred under hydrogen atmosphere (at atmospheric pressure) for 20 hours. Subsequently, 100 ml methanol is added and the catalyst is removed by filtering. The product is then obtained by concentrating the methanolic solution.

Analysis for $C_{19}H_{15}F_2N_3O_2$

| % C(calcd/found) | % H | % N |
|---|---|---|
| 64.22/64.09 | 4.25/4.29 | 11.83/12.01 |

Yield: 88% Melting temp.: 248–251° C.

Example 53

1-(2,3-Dichlorophenyl)-3-((4'-aminophenoxy)-phenyl)-urea

The title compound was prepared from compound 6 by an analogous procedure to that described in Example 52.

Analysis for $C_{19}H_{15}Cl_2N_3O_2$

| % C(calcd/found) | % H | % N | % Cl |
|---|---|---|---|
| 58.78/58.45 | 3.89/3.94 | 10.82/10.78 | 18.26/18.11 |

Yield: 91% Melting temp.: 201–204° C.

Example 54

1-(2,6-Dimethylphenyl)-3-((4'-aminophenoxy)-phenyl)-urea

The title compound was prepared from compound 12 by an analogous procedure to that described in Example 52.

Analysis for $C_{21}H_{21}N_3O_2$

| % C(calcd/found) | % H | % N |
|---|---|---|
| 72.60/72.45 | 6.09/6.13 | 12.10/12.02 |

Yield: 85% Melting temp.: 225–227° C.

Example 55
1-(2,6-Di(methylethyl)-phenyl)-3-((4'-aminophenoxy)-phenyl)-urea

The title compound was prepared from compound 14 by an analogous procedure to that described in Example 52.

$^1$H-NMR (CDCl$_3$): 1.15(d, 6H, 2xCH$_3$); 3.15(hept., 2H, 2xCH); 4.86(s, 2H, NH); 6.57(d, 2H, H-arom.); 6.72(d, 2H, H-arom.); 6.81(d, 2H, H-arom.); 7.10–1.28(m, 3H, H-arom.); 7.36(d, 2H, H-arom.); 7.56(s, 1H, HN); 8.58(br.s., 1H, NH).

$^{13}$C-NMR (CDCl$_3$): 23.43(2xCH$_3$); 27.93(2xCH); 114.63 (CH-arom.); 117.55(CH-arom.); 119.09(CH-arom.); 199.43 (CH-arom.); 122.79(CH-arom.); 127.11(CH-arom.); 127.11 (CH-arom.); 132.40, 134.86, 144.77, 146.61, 146.89, 152.88 (C-arom.); 154.36(C=O).

Analysis for C$_{25}$H$_{29}$N$_3$O$_2$

| % C(calcd/found) | % H | % N |
|---|---|---|
| 74.41/74.54 | 7.24/7.33 | 10.41/10.34 |

Yield: 90% Melting temp.: 219–221° C.

Example 56
1-(2,4-Difluorophenyl)-3-((4'-aminophenylthio)-phenyl)-urea

The title compound was prepared from compound 27 by an analogous procedure to that described in Example 52.

Analysis for C$_{19}$H$_{15}$F$_2$N$_3$OS

| % C(calcd/found) | % H | % N | % S |
|---|---|---|---|
| 61.44/61.56 | 4.07/4.18 | 11.31/11.15 | 8.63/8.51 |

Yield: 79% Melting temp.: exceeding 300° C.

Example 57
1-(2,3-Dichlorophenyl)-3-((4'-aminophenylthio)-phenyl)-urea

The title compound was prepared from compound 32 by an analogous procedure to that described in Example 52.

Analysis for C$_{19}$H$_{15}$Cl$_2$N$_3$OS

| % C (calcd/found) | % H | % N | % Cl | S % |
|---|---|---|---|---|
| 56.44/56.35 | 3.74/3.80 | 10.39/10.41 | 17.54/17.57 | 7.93/7.59 |

Yield: 88% Melting temp.: 259–261° C.

Example 58
1-(2,6-Dimethylphenyl)-3-((4'-aminophenylthio)-phenyl)-urea

The title compound was prepared from compound 40 by an analogous procedure to that described in Example 52.

Analysis for C$_{21}$H$_{21}$N$_3$OS

| % C(calcd/found) | % H | % N | % S |
|---|---|---|---|
| 69.39/69.32 | 5.82/5.93 | 11.56/11.49 | 8.28/8.54 |

Yield: 94% Melting temp.: 198–202° C.

Example 59
1-(2,6-Di-(methylethyl)-phenyl-3-((4'-aminophenylthio)-phenyl)-urea The title compound was prepared from compound 42 by an analogous procedure to that described in Example 52.

Analysis for C$_{25}$H$_{29}$N$_3$OS

| % C(calcd/found) | % H | % N | % S |
|---|---|---|---|
| 71.56/71.55 | 6.97/6.89 | 10.01/10.11 | 7.64/7.58 |

Yield: 83% Melting temp.: 267–271° C.

Tests

The biological activity of the substances was evaluated based on the in vitro inhibition of acylCoa:cholesterol acyltransferase (ACAT) activity. The enzyme was obtained from the microsomal fraction of rat liver cells and rabbit intestinal mucosa of animals fed with cholesterol. The substrates for the enzyme reaction included exogenous oleoyl co-enzyme A and endogenous cholesterol. $^{14}$C-oleoyl co-enzyme A conversion to $^{14}$C-cholesteryl oleate was monitored. From the mixture of extracted lipids, cholesteryl oleate was separated using thin-layer chromatography, and was quantified radiometrically. ACAT specific activity was expressed as the amount of cholesteryl oleate formed per minute per mg microsomal protein.

Table 1 shows percentages of ACAT inhibition in the rat liver and the rabbit intestinal mucosa at various concentrations of the substances tested. Efficiency was calculated as compared to enzyme activity measured in the presence of 1% dimethylsulfoxide used as the solvent to prepare solutions of the substances tested.

TABLE 1

Inhibitory effect of the compounds on rat liver and rabbit intestinal mucosa ACAT activity

| No | Efficiency liver | (%) mucosa | Concentration ($\mu$M) |
|---|---|---|---|
| 1 | 15 | 32 | 2 |
| 2 | 37 | 55 | 2 |
| 3 | 49 | 58 | 2 |
| 4 | 0 | 42 | 2 |
| 5 | 0 | 0 | 2 |
| 6 | 58 | 51 | 2 |
| 7 | 20 | 25 | 2 |
| 8 | 0 | 0 | 2 |
| 9 | 0 | 0 | 2 |
| 10 | 0 | 0 | 2 |
| 11 | 0 | 0 | 2 |
| 12 | 41 | 65 | 2 |
| 13 | 0 | 0 | 2 |
| 14 | 50 | 67 | 2 |
| 15 | 46 | 42 | 2 |
| 16 | 38 | 45 | 2 |
| 17 | 25 | 18 | 2 |
| 18 | 26 | 34 | 2 |
| 19 | 0 | 0 | 2 |

TABLE 1-continued

Inhibitory effect of the compounds on rat liver and rabbit intestinal mucosa ACAT activity

| No | Efficiency liver | (%) mucosa | Concentration (μM) |
|---|---|---|---|
| 20 | 11 | 17 | 2 |
| 21 | 14 | 22 | 2 |
| 22 | 0 | 12 | 2 |
| 23 | 43 | 58 | 2 |
| 24 | 0 | 34 | 2 |
| 25 | 0 | 23 | 2 |
| 26 | 25 | 27 | 2 |
| 27 | 16 | 23 | 2 |
| 28 | 0 | 16 | 2 |
| 29 | 11 | 25 | 2 |
| 30 | 20 | 26 | 2 |
| 31 | 12 | 21 | 2 |
| 32 | 0 | 0 | 2 |
| 33 | 12 | 16 | 2 |
| 34 | 15 | 21 | 2 |
| 35 | 0 | 20 | 2 |
| 36 | 0 | 0 | 2 |
| 37 | 27 | 31 | 2 |
| 38 | 21 | 32 | 2 |
| 39 | 19 | 31 | 2 |
| 40 | 23 | 34 | 2 |
| 41 | 18 | 27 | 2 |
| 42 | 88 | 71 | 2 |
| 43 | 25 | 38 | 2 |
| 44 | 34 | 45 | 2 |
| 45 | 23 | 25 | 2 |
| 46 | 48 | 46 | 2 |
| 47 | 45 | 36 | 2 |
| 48 | 53 | 35 | 2 |
| 49 | 24 | 36 | 2 |
| 50 | 16 | 31 | 2 |
| 51 | 45 | 56 | 2 |
| 52 | 53 | 64 | 2 |
| 53 | 55 | 46 | 2 |
| 54 | 38 | 62 | 2 |
| 55 | 68 | 64 | 2 |
| 56 | 22 | 25 | 2 |
| 57 | 15 | 26 | 2 |
| 58 | 21 | 29 | 2 |
| 59 | 56 | 67 | 2 |

Industrial Applicability

The compounds according to the invention and the method of preparing thereof can be used in pharmaceutical production to make preparations with inhibitory effect on the enzyme acyl co-enzyme A and on cholesterol absorption in hypercholesterolemia.

What is claimed is:

1. 1,3-Disubstituted ureas of general formula 1,

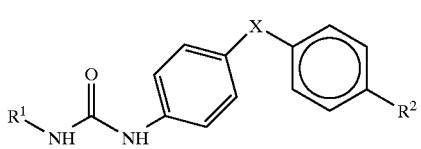

I

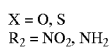

X = O, S
R$_2$ = NO$_2$, NH$_2$ wherein R$^1$ is 2-fluorophenyl, 2,4-difluorophenyl, 2,5-difluorophenyl, 2,6-difluorophenyl, 2,3-dichlorophenyl, 2,6-dichlorophenyl, 3,5-dichlorophenyl, 2-methylphenyl, 4-methylphenyl, 2,4-dimethylphenyl, 2,6-dimethylphenyl, 3,5-dimethylphenyl, 2,6-di(methylethyl)phenyl, 2-trifluoromethylphenyl, 3-trifluoromethylphenyl, 2-pyridyl, 3-pyridyl, 4-pyridyl, 1-naphthyl, 2-naphthyl, or 1-adamantyl, R$^2$ is nitro, and X=O; or R$^1$ is 4-nitrophenyl, 2-fluorophenyl, 4-fluorophenyl, 2,4-difluorophenyl, 2,5-difluorophenyl, 2,6-difluorophenyl, 2-chlorophenyl, 4-chlorophenyl, 2,3-dichlorophenyl, 2,4-dichlorophenyl, 2,6-dichlorophenyl, 3,4-dichlorophenyl, 3,5-dichlorophenyl, 2-methylphenyl, 4-methylphenyl, 2,4-dimethylphenyl, 2,6-dimethylphenyl, 3,5-dimethylphenyl, 2,6-(di (methylethyl)phenyl, 2-trifluoromethylphenyl, 3-trifluoromethylphenyl, 4-trifluoromethylphenyl, 2-pyridyl, 3-pyridyl, 4-pyridyl, 1-naphthyl, 2-naphthyl, or 1-adamantyl, R$^2$ is nitro, and X=S; or R$^1$ is 2,4-difluorophenyl, 2,3-dichlorophenyl, 2,6-dimethylphenyl, or 2,6-di(methylethyl)-phenyl, R$^2$ is amino, and X=O, S.

2. A method of preparing 1,3-disubstituted ureas of general formula I according to claim 1, comprising treating an amine of general formula II,

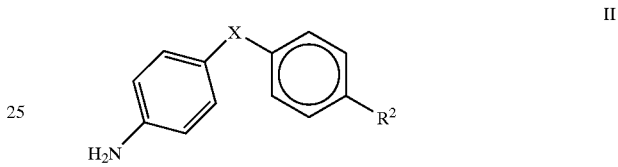

II wherein R$^2$ and X have the above defined meanings, with an isocyanate of general formula III,

III wherein R$^1$ has the above defined meaning, said isocyanate optionally being formed in situ from appropriate reactants, thus giving the above defined urea.

3. The method of claim 2, wherein when said isocyanate is formed in situ, the reaction is carried out in toluene at about 80° C.

4. The method of claim 2, wherein the obtained 1,3-disubstituted urea of general formula I wherein R$^2$ means nitro, is treated with hydrogen in the presence of palladium catalyst to reduce the nitro group to the amino group.

5. A method of inhibiting the effect on the acyl co-enzyme A: cholesterol acyltransferase (ACAT) enzyme comprising administering to a patient in need of said inhibiting effect, a 1,3-disubstituted ureas of general formula I

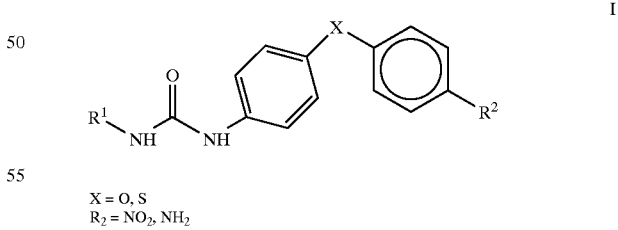

I

X = O, S
R$_2$ = NO$_2$, NH$_2$ wherein R$^1$ is 2-fluorophenyl, 2,4-difluorophenyl, 2,5-difluorophenyl, 2,6-difluorophenyl, 2-chlorophenyl, 2,3-dichlorophenyl, 2,6-dichlorophenyl, 3,5-dichlorophenyl, 2-methylphenyl, 4-methylphenyl, 2,4-dimethylphenyl, 2,6-dimethylphenyl, 3,5-dimethylphenyl, 2,6-di(methylethyl) phenyl, 2-trifluoromethylphenyl, 3-trifluoromethylphenyl, 4-trifluoromethylphenyl, 2-pyridyl, 3-pyridyl, 4-pyridyl, 1-naphthyl, 2-naphthyl, or 1-adamantyl, R$^2$ is nitro and X=O; or $R^1$ is 4-nitrophenyl, 2-fluorophenyl, 4-fluorophenyl, 2,4-difluorophenyl, 2,5-difluorophenyl, 2,6-difluorophenyl, 2-chlorophenyl, 4-chlorophenyl, 2,3-dichlorophenyl, 2,4-dichlorophenyl, 2,6-dichlorophenyl, 3,4-dichlorophenyl, 3,5-dichlorophenyl, 2-methylphenyl, 4-methylphenyl, 2,4-dimethylphenyl, 2,6-dimethylphenyl, 3,5-dimethylphenyl, 2,6-di(methylethyl)phenyl, 2-trifluoromethylphenyl, 3-trifluoromethylphenyl, 4-trifluoromethylphenyl, 2-pyridyl, 3-pyridyl, 4-pyridyl, 1-naphthyl, 2-naphthyl, or 1-adamantyl, $R^2$ is nitro, and X=S; or $R^1$ is 2,4-difluorophenyl, 2,3-dichlorophenyl, 2,6-dimethylphenyl, or 2,6-di(methylethyl)-phenyl, $R^2$ is amino, and X=O, S.

\* \* \* \* \*

UNITED STATES PATENT AND TRADEMARK OFFICE
CERTIFICATE OF CORRECTION

PATENT NO. : 6,444,691 B1
DATED : September 3, 2002
INVENTOR(S) : Oremus et al.

It is certified that error appears in the above-identified patent and that said Letters Patent is hereby corrected as shown below:

<u>Title page,</u>
Item [73], Assignee should read:

-- [73] Assignee: Slovakofarma, a.s., Hlohovec (SK) --

Signed and Sealed this

Fourteenth Day of January, 2003

JAMES E. ROGAN
*Director of the United States Patent and Trademark Office*